United States Patent [19]

Ohnuma et al.

[11] Patent Number: 4,968,667
[45] Date of Patent: Nov. 6, 1990

[54] 1,1-DIMETHYL-3-HYDROXYMETHYLINDANE AND PERFUMERY COMPOSITION COMPRISING THE SAME

[75] Inventors: Hiroaki Ohnuma, Ichikai; Yoshiaki Fujikura, Utsunomiya; Manabu Fujita, Kashiwa; Nao Toi, Sakura, all of Japan

[73] Assignee: Kao Corporation, Tokyo, Japan

[21] Appl. No.: 421,129

[22] Filed: Oct. 13, 1989

[30] Foreign Application Priority Data

Oct. 20, 1988 [JP] Japan ................ 63-265017

[51] Int. Cl.$^5$ ............................ A61K 7/46
[52] U.S. Cl. .......................... 512/14; 568/808
[58] Field of Search ............ 568/808; 512/14

[56] References Cited

U.S. PATENT DOCUMENTS

| | | | |
|---|---|---|---|
| 2,857,433 | 10/1958 | Bruson et al. | 568/808 |
| 3,660,311 | 5/1972 | Wight | 512/14 |
| 3,663,627 | 5/1972 | Juby et al. | 568/808 |
| 4,532,357 | 7/1985 | Van Loveren et al. | 512/14 |

OTHER PUBLICATIONS

Staab et al, Chem. Ber., vol. 111, pp. 2905–2981 (1978).

*Primary Examiner*—James H. Reamer
*Attorney, Agent, or Firm*—Oblon, Spivak, McClelland, Maier & Neustadt

[57] ABSTRACT

A novel 1,1-dimethyl-3-hydroxymethylindane represented by formula (I) is disclosed.

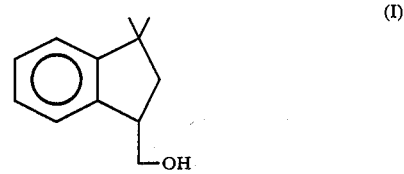

A perfumery composition comprising the same is also disclosed.

The compound represented by formula (I) of the present invention possesses a lasting floral, fruity, herbal, and woody odor based on a rosy tone. The perfumery compositions comprising Compound (I) can widely be used as a perfumery material for perfumes, soaps, shampoos, room flavors, detergents, and the like.

3 Claims, No Drawings

1,1-DIMETHYL-3-HYDROXYMETHYLINDANE AND PERFUMERY COMPOSITION COMPRISING THE SAME

BACKGROUND OF THE INVENTION

1. Field of the Invention:

The present invention relates to novel 1,1-dimethyl-3-hydroxymethylindane of the following formula (I):

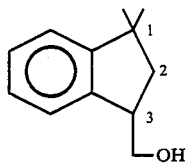

This invention also relates to a perfumery composition comprising the same.

2. Description of the Background Art:

There have conventionally been known many perfumery compounds among compounds having an indane structure. Given as examples of these perfumery compounds are those having a musky odor, e.g. 1,1,2,3,3,8-hexamethyl-6-oxa-2,3,5,6,7,8-hexahydro-1H-benzo[f]indene (U.S. Pat. No. 4,162,256), 6-acetyl-1,1,2,3,3,5-hexamethylindane (FR Patent No. 1,392,804), 4-acetyl-1,1-dimethyl-6-tert-butylindane (U.S. Pat. No. 3,078,319); those having an indole-like odor, e.g. 4,4a,5,9b-tetrahydroindeno[1,2:d]-m-dioxine (DE Patent No. 714,645); those having a geranium- or magnolia-like odor, e.g. 2,4-dimethyl-4,4a,5,9b-tetrahydroindeno[1,2:d]-m-dioxine (FR Patent No. 1,577,817), and the like.

Since an odor of a compound is quite different from an odor of another component having very similar but slightly different chemical structure, it is very important to synthesize various compounds and examine their odors for producing new perfumeries.

In view of this, the present inventors have synthesized various compounds having an indane structure and investigated their odors or fragrances and their application as perfumes. As a result, the inventors have found that 1,1-dimethyl-3-hydroxymethylindane of formula (I) possessed an excellent odor, and also found that it was useful as a perfumery component. This finding has led to the completion of this invention.

SUMMARY OF THE INVENTION

Accordingly, an object of this invention is to provide 1,1-dimethyl-3-hydroxymethylindane of formula (I):

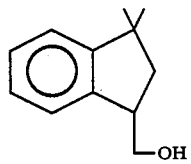

and also to provide a perfumery composition comprising the same.

Other objects, features and advantages of the invention will hereinafter become more readily apparent from the following description.

DETAILED DESCRIPTION OF THE INVENTION AND PREFERRED EMBODIMENTS

The compound (I) of this invention can be produced, for example, according to the following reaction scheme:

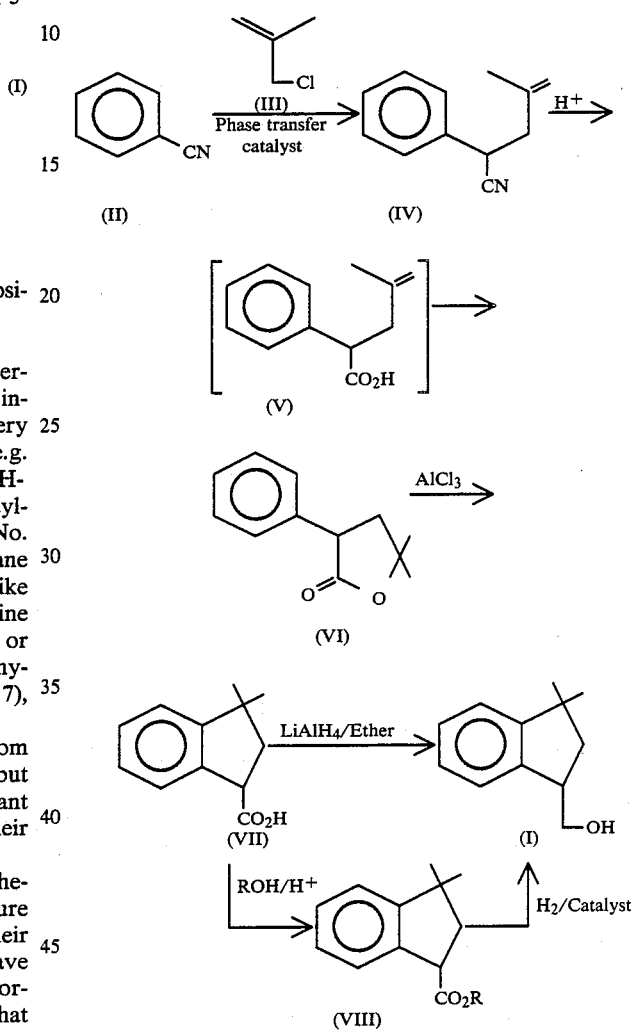

wherein R represents an alkyl group.

According to a known process [Makosza, Org. Synth.,55, 91 (1976)], phenylacetonitrile [Compound (II) in the above reaction scheme] is recited with methallyl chloride [Compound (III)] in the presence of a phase transfer catalyst to produce 4-methyl-2-phenyl-4-pentenenitrile [Compound (IV)]. Given as examples of a phase transfer catalyst are triethylbenzylammonium chloride, tetra-n-butylammonium bromide, and the like. Phenylacetonitrile [Compound (II)] used in the above reaction is 1–10 equivalent to methallyl chloride [Compound (III)], with a range of 2–10 equivalent being particularly preferable. A preferable amount of a phase transfer catalyst to be used is in the range of a 0.001–0.1 equivalent to methallyl chloride, with a 0.005–0.05 equivalent being particularly preferable. It is desirable that the reaction be carried out at a temperature of 5°–50° C., especially at 5°–30° C., in the presence of water and a caustic alkali.

The hydrolysis and cyclization reaction of 4-methyl-2-phenyl-4-pentenenitril [Compound (IV)] is then carried out by a single operation using an acid such as aqueous hydrochloric acid, aqueous sulfuric acid, or the like to produce 4,4-dimethyl-2-phenyl-4-butanolide [a lactone, Compound (VI)]. The reaction can be carried out either without or using a solvent such as an alcohol, e.g. methanol, ethanol; an organic acid, e.g. acetic acid, formic acid; and the like.

The lactone [Compound (VI)] thus produced is reacted with a Lewis acid, e.g. aluminum chloride, aluminum bromide, to obtain 3-carboxy-1,1-dimethylindane [a carboxylic acid, Compound (VII)]. A preferable amount of Lewis acid used is in the range of a 0.1–3.0 equivalent to the intermediate lactone [Compound (VI)], with the range of a 1–3.0 equivalent being particularly preferable. Examples of preferable organic solvent used in the above reaction are dichloromethane, 1,2-dichloroethane, chloroform, and the like. The reaction is carried out at a temperature of 0°–50° C., preferably at 0°–40° C.

Compound (I) can be produced from the carboxylic acid [Compound (VII)], for example, by reducing the carboxylic acid using a reducing agent, e.g. lithium aluminium hydride, in an ether solution such as diethylether, tetrahydrofuran, or the like.

Alternatively, Compound (I) can be produced from the carboxylic acid [Compound (VII)], for example, by refluxing the carboxylic acid and an alcohol, e.g. methanol, ethanol, under heating in the presence of an acid, e.g. sulfuric acid, p-toluenesulfonic acid, to produce 3-alkoxycarbonyl-1,1-dimethylindane [an ester, Compound (VIII)], which is catalytically hydrogenated in the presence of a catalyst, e.g. copper-chrome, copper-zinc. The hydrogenation reaction can be performed without a solvent. However, a saturated hydrocarbon, e.g. n-hexane; an alcohol, e.g. methanol, ethanol; or the like may be used as a solvent.

It is desirable that the amount of the catalyst used be 1–20% by weight of the ester [Compound (VIII)] and the hydrogen pressure be 20–150 atoms. The reaction can usually be performed at 80°–300° C. A temperature of 150°–250° C. is preferable from the aspect of shortening the reaction time and reducing production of by-products.

The compound of formula (I) [Compound (I)] of the present invention possesses a lasting floral, fruity, herbal, and woody odor based on a rosy tone. The perfumery compositions comprising Compound (I) can widely be used as a perfumery material for perfumes, soaps, shampoos, room flavors, detergents, and the like.

Other features of the invention will become apparent in the course of the following description of the exemplary embodiments for preparing the intermediates and the compound of the present invention. It should be understood that these embodiments are given for illustration of the invention and are not intended to be limiting thereof.

EXAMPLES

Reference Example 1

Synthesis of 4-methyl-2-phenyl-4-pentenenitrile [Compound (IV)]

To a mixed solution of 1,580 g (13.5 mol) of phenylacetonitrile, 11.3 g (5.0 mmol) of triethylbenzylammonium chloride, and 1,200 ml of 50% aqueous sodium hydroxide was added dropwise 410 g (4.5 mol) of methallyl chloride over 2 hours, while vigorously stirring and maintaining the temperature at 20°–30° C. After the addition, the mixture was stirred at the same temperature for one hour. 1,700 ml of water was added to the reaction mixture and the mixture was separated into an organic layer and a water layer. The organic layer was washed twice with 300 ml of saturated brine, once with 50 ml of 10% hydrochloric acid, and further twice with 100 ml of saturated brine, and dried over anhydrous sodium sulfate. The solvent was evaporated from the organic layer. The residue was distilled under reduced pressure to obtain 670 g (3.9 mol) of the target Compound (IV) at a yield of 87% for the feed methallyl chloride.

Boiling Point: 126°–130° C./10 mmHg

Elemental Analysis: for $C_{12}H_{13}N$ Found: C 84.29, H 7.51 Calculated: C 84.17, H 7.65

MS (Relative Intensity) 171 ($M^+$, 24), 154 (6), 143 (26), 129 (13), 116 (58), 103 (11), 89 (12), 77 (11), 55 (100), 39 (29)

IR (neat, $cm^{-1}$) 3084, 2924, 2244, 1652, 1498, 1456, 902, 754, 700

$^1$H-NMR (Solvent: CDCl$_3$, Internal standard method: TMS, δ) 7.32(5H, s), 5.0–4.7(2H, m), 3.92(1H, t, 8), 2.55(2H, d), 1.77(3H, s)

Reference Example 2

Synthesis of 4,4-dimethyl-2-phenyl-4-butanolide [Compound (VI)]

385 g (2.2 mol) of 4-methyl-2-phenyl-4-pentenenitrile [Compound (IV)] was refluxed under heating in 530 ml of water and 390 ml of concentrated sulfuric acid for 3 hours. The mixture was cooled to room temperature and 900 ml of water was added to the mixture. White crystals produced were separated by filtration under reduced pressure. The white crystals were washed twice with 500 ml of hexane and twice with 500 ml of warm water. The solvent was evaporated from the washed white crystals to obtain 300 g (1.6 mol) of the target Compound (VI) at a yield of 70%.

Melting Point: 66.0°–66.8° C.

Elemental Analysis: for $C_{12}H_{14}O_2$ Found: C 75.85, H 7.44; Calculated: C 75.76, H 7.42;

MS (Relative Intensity) 190 ($M^+$, 2), 175 (6), 146 ($M^+$—CO$_2$, 54), 131 (100), 116 (6), 104 (16), 91 (34), 77 (12), 51 (12), 43 (83)

IR (KBr tablet, $cm^{-1}$) 2984, 1776, 1378, 1264, 1142, 958, 706, 692, $^1$H-NMR (Solvent: CDCl$_3$, Internal standard method: TMS, δ) 7.35–7.20(5H, m), 4.00(1H, dd, 9, 12), 2.53(1H, dd, 9, 13), 2.18(1H, dd, 12, 13), 1.49(3H, s), 1.44(3H, s)

$^{13}$C-NMR (CDCl$_3$, TMS, δ) 176.2(s), 137.3(s), 128.6(d), 128.0(d), 127.2(d), 81.8(s), 46.7(d), 43.7(t), 28.7(q), 26.7(q)

Reference Example 3

Synthesis of 3-carboxy-1,1-dimethylindane [Compound (VII)]

117 g (0.615 mol) of 4,4-dimethyl-2-phenyl-4-butanolide [Compound (VI)] dissolved in 200 ml of 1,2-dichloroethane was added to 164 g (1.23 mol) of anhydrous aluminium chloride dissolved in 200 ml of 1,2-dichloroethane under ice-cooling for one hour. The mixture was stirred for 2 hours, charged into 1,000 ml of ice water, and extracted with 500 ml of chloroform. The organic layer was washed twice with 500 ml of water and dried over anhydrous sodium sulfate. The solvent was evaporated and the residue was distilled under reduced pressure to produce 96 g of the target Compound (VII) at a yield of 82% for the feed lactone.

Boiling Point: 152°–153° C./3 mmHg

Elemental Analysis: for $C_{12}H_{14}O_2$ Found: C 75.69, H 7.41; Calculated: C 75.76, H 7.42

MS (Relative Intensity) 190 (M+, 44), 175 (100), 145 (26), 129 (70), 115 (15), 91 (11), 77 (7), 63 (5), 51 (7), 39(6)

IR (Liquid film, cm$^{-1}$) 3028, 2960, 1710, 1482, 1418, 1306, 1228, 928, 762

$^1$H-NMR (Solvent: CDCl$_3$, Internal standard method: TMS, δ) 12.07(1H, brs), 7.40(1H, d, 7), 7.3–7.1(3H, m), 4.13(1H, t, 8), 2.32(1H, dd, 8, 13), 2.23(1H, dd, 8, 13), 1.38(3H, s), 1.23(3H, s)

$^{13}$C-NMR (CDCl$_3$, TMS, δ) 180.9(s), 152.4(s), 138.4(s), 128.0(d), 126.8(d), 125.0(d), 122.3(d), 47.8(d), 44.1(t), 43.5(s), 29.5(q), 29.0(q)

EXAMPLE 1

Synthesis of 1,1-dimethyl-3-hydroxymethylindane [Compound (I)]

A mixed solution of 100 g (0.53 mol) of 3-carboxy-1,1-dimethylindane [Compound (VII)] and 300 ml of ether was added dropwise to 25 g (0.66 mol) of lithium aluminium hydride dissolved in 300 ml of ether under ice-cooling for one hour. After the addition, the mixture was mildly refluxed under heating for one hour. To the reaction mixture was added 25 ml of water, 25 ml of 15% aqueous sodium hydroxide, and 75 ml of water in this order to hydrolyze excess lithium aluminium hydride. White precipitates produced were eliminated by filtration under reduced pressure. The filtrate was distilled under reduced pressure to obtain 89 g (0.51 mol) of the target Compound (I) at a yield of 96%.

Boiling Point: 108° C./2.5 mmHg

Elemental Analysis: for $C_{12}H_{16}O$ Found: C 81.75, H 9.17; Calculated: C 81.77, H 9.11

MS (Relative Intensity) 176 (M+, 28), 161 (12), 145 (100), 143 (29), 128 (23), 117 (13), 105 (6), 91 (11), 77 (5)

IR (Liquid film, cm$^{-1}$) 3370, 2956, 2866, 1482, 1026, 759, 744

$^1$H-NMR (CDCl$_3$, TMS, δ) 7.3–7.1(4H, m), 4.0–3.8(2H, m), 3.41(1H, m), 2.13(1H, dd, 7, 12), 1.78(1H, dd, 7, 12), 1.54(1H, brs), 1.36(3H, s), 1.21(3H, s)

$^{13}$C-NMR (CDCl$_3$, TMS, δ) 153.2(s), 142.4(s), 127.2(d), 126.4(d), 123.8(d), 122.3(d), 66.1(t), 44.9(d), 44.9(t), 43.0(s), 29.9(q), 29.3(q)

EXAMPLE 2

Synthesis of 1,1-dimethyl-3-hydroxymethylindane [Compound (I)]

(1) 100 g (0.53 mol) of 3-carboxy-1,1-dimethylindane [Compound (VII)] was added to a mixture of 60 ml of methanol and 500 ml of dichloroethane. The mixture was refluxed under heating for 10 hours in the presence of 1.5 ml of sulfuric acid as a catalyst. The reaction mixture was allowed to stand until it was cooled and diluted with water to separate an organic layer. The organic layer was washed with aqueous sodium bicarbonate and dried. The solvent was evaporated and the residue was distilled under reduced pressure to obtain 103 g (0.50 mol) of 1,1-dimethyl-3-methoxycarbonylindane [Compound (VIII)] at a yield of 95%.

Boiling Point: 118° C./5 mmHg

Elemental Analysis: for $C_{13}H_{16}O_2$ Found: C 76.41, H 7.92; Calculated: C 76.44, H 7.89

MS (Relative Intensity) 204 (M+, 40), 189 (71), 157 (12), 145 (76), 130 (21), 129 (100), 128 (17), 115 (12), 91 (8)

IR (Liquid film, cm$^{-1}$) 2956, 1743, 1482, 1167, 762

$^1$H-NMR (CDCl$_3$, TMS, δ) 7.4–7.1(4H, m), 4.10(1H, t, 8), 3.75(3H, s), 2.31(1H, dd, 8, 13), 2.19(1H, dd, 8, 13), 1.37(3H, s), 1.21(3H, s)

$^{13}$C-NMR (CDCl$_3$, TMS, δ) 174(s), 152(s), 139(s), 128(d), 127(d), 125(d), 122(d), 52(q), 48(d), 44(t), 43(s), 29.5(q), 29(q)

(2) A mixture of 50 g (0.24 mol) of 1,1-dimethyl-3-methoxycarbonylindane [Compound (VIII)] obtained above and 5 g of a copper-chrome catalyst was placed in a 100 ml autoclave. After inner air was displaced by hydrogen the mixture was heated at an initial hydrogen pressure of 100 kg/cm$^2$. The reaction temperature reached 230° C. 30 minutes after the heating was started. The absorption of hydrogen terminated when the reaction was continued at this temperature for 8 hours. After the reaction, mixture was cooled, the pressure was released, and the catalyst was separated by filtration. Filtrate was distilled under reduced pressure to produce 35 g (0.20 mol) of the target Compound (I) at a yield of 82%.

EXAMPLE 3

Lasting lemon type perfume

|  | Part by weight |
|---|---|
| Limonene | 810 |
| Iso-cyclocitral *1 | 10 |
| Nerol | 20 |
| Fruitate *2 | 5 |
| Geranylnitrile | 50 |
| Citronellal | 5 |
| Methoxy Citronellal | 10 |
| Total | 910 |

*1 Iso-cyclocitral: 3,5,6-trimethyl-3-cyclohexene-1-carboaldehyde
*2 Fruitate (Trademark, manufactured by Kao Corporation): Ethyl[5.2.1.0 2,6]tricyclodecane-2-carboxylate To 910 parts by weight of the above ingredients was added 90 parts by weight of 1,1-dimethyl-3-hydroxymethylindane to obtain a lasting lemon type perfume having excellent fresh feeling.

Obviously, numerous modifications and variations of the present invention are possible in light of the above teachings. It is therefore to be understood that within the scope of the appended claims, the invention may be practiced otherwise than as specifically described herein.

What is claimed is:

1. A perfumery composition comprising 1,1-dimethyl-3-hydroxymethylindane represented by the following formula (I):

and a perfumery carrier compatible with a floral, fruity herbal or woody aroma.

2. A perfumery composition comprising the compound of formula (I):

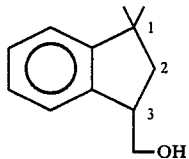

(I)

and limonene.

3. A process for enhancing the floral, fruity, herbal or woody aroma of a perfumery composition comprising the step of adding to said perfumery composition an aroma enhancing quantity of 1,1-dimethyl-3-hydroxymethylindane represented by the formula (I):

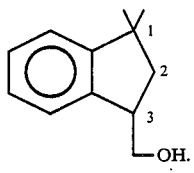

(I)

* * * * *